United States Patent
Giron et al.

(10) Patent No.: US 12,232,593 B2
(45) Date of Patent: Feb. 25, 2025

(54) METHOD FOR SHAPING AN APPLICATOR FOR APPLYING A COSMETIC COMPOSITION

(71) Applicant: L'OREAL, Paris (FR)

(72) Inventors: Franck Giron, Chevilly Larue (FR); Henri Samain, Chevilly Larue (FR)

(73) Assignee: L'OREAL, Paris (FR)

( * ) Notice: Subject to any disclaimer, the term of this patent is extended or adjusted under 35 U.S.C. 154(b) by 387 days.

(21) Appl. No.: 17/617,170

(22) PCT Filed: Jun. 25, 2020

(86) PCT No.: PCT/EP2020/067923
§ 371 (c)(1),
(2) Date: Dec. 7, 2021

(87) PCT Pub. No.: WO2020/260515
PCT Pub. Date: Dec. 30, 2020

(65) Prior Publication Data
US 2022/0256996 A1   Aug. 18, 2022

(30) Foreign Application Priority Data
Jun. 28, 2019 (FR) ........................ 1907111

(51) Int. Cl.
*A61B 5/00* (2006.01)
*A45D 33/38* (2006.01)
*A45D 44/00* (2006.01)

(52) U.S. Cl.
CPC ............ *A45D 44/00* (2013.01); *A45D 33/38* (2013.01); *A61B 5/0064* (2013.01);
(Continued)

(58) Field of Classification Search
CPC ..................................... A61B 5/0064
See application file for complete search history.

(56) References Cited

U.S. PATENT DOCUMENTS

| 4,804,719 A | 2/1989 | Weaver et al. |
| 4,999,418 A | 3/1991 | Krutak et al. |

(Continued)

FOREIGN PATENT DOCUMENTS

| CA | 2453191 | * | 5/2010 |
| CN | 106175037 A | | 12/2016 |

(Continued)

OTHER PUBLICATIONS

International Search Report (ISR) for PCT/EP2020/067923 mailed Oct. 1, 2020 (3 pages).

(Continued)

*Primary Examiner* — Edmund H Lee
(74) *Attorney, Agent, or Firm* — Shumaker, Loop & Kendrick, LLP

(57) ABSTRACT

Method for shaping an applicator for applying a cosmetic composition to a predefined region of the keratin materials of a user. The applicator defining an application surface. The method using a shaping system comprising one or more movable elements and topographical data from an operation of acquiring, preferably digitally, the topography of at least a portion of said predefined region, in which method the shaping system automatically positions the one or more movable elements at least according to the topographical data, the positioning of the one or more movable elements imposing a shape to the application surface of the applicator.

27 Claims, 5 Drawing Sheets

(52) U.S. Cl.
CPC ............... *A45D 2200/1018* (2013.01); *A45D 2200/1036* (2013.01); *A45D 2200/25* (2013.01)

(56) References Cited

U.S. PATENT DOCUMENTS

| | | | |
|---|---|---|---|
| 5,030,708 | A | 7/1991 | Krutak et al. |
| 5,032,670 | A | 7/1991 | Parham et al. |
| 5,043,376 | A | 8/1991 | Sharma et al. |
| 5,102,980 | A | 4/1992 | Krutak et al. |
| 5,104,913 | A | 4/1992 | Sharma et al. |
| 5,106,942 | A | 4/1992 | Krutak et al. |
| 5,194,463 | A | 3/1993 | Kutak et al. |
| 5,281,659 | A | 1/1994 | Weaver et al. |
| 6,053,026 | A * | 4/2000 | Nardiello ............... B21D 37/02 72/413 |

FOREIGN PATENT DOCUMENTS

| | | | |
|---|---|---|---|
| EP | 0938887 | A | 9/1999 |
| EP | 1048282 | A1 | 11/2000 |
| EP | 1410785 | A1 | 4/2004 |
| EP | 2460435 | A1 | 6/2012 |
| FR | 3072546 | A1 | 4/2019 |
| WO | 1992//007913 | A1 | 5/1992 |
| WO | 2002/036083 | A1 | 5/2002 |
| WO | 2015/097613 | A1 | 7/2015 |

OTHER PUBLICATIONS

Written Opinion for PCT/EP2020/067923 mailed Oct. 1, 2020 (5 pages).

* cited by examiner

[Fig 1]
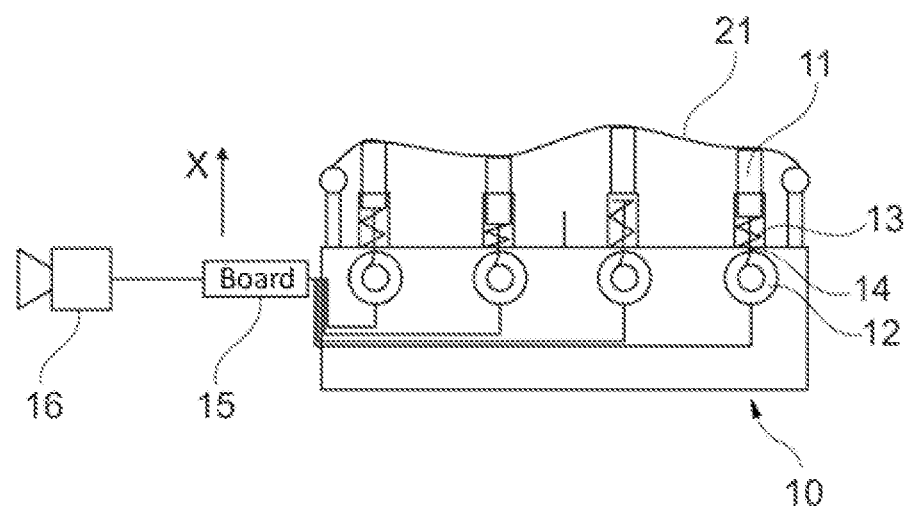
[Fig 2]
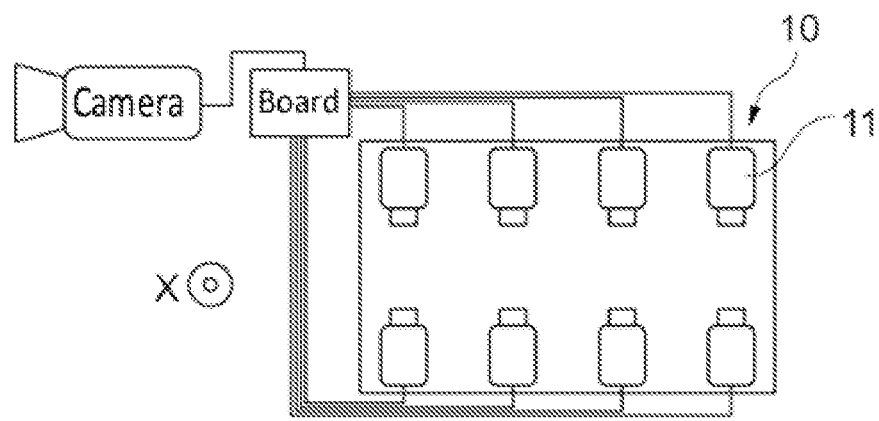

[Fig 3]
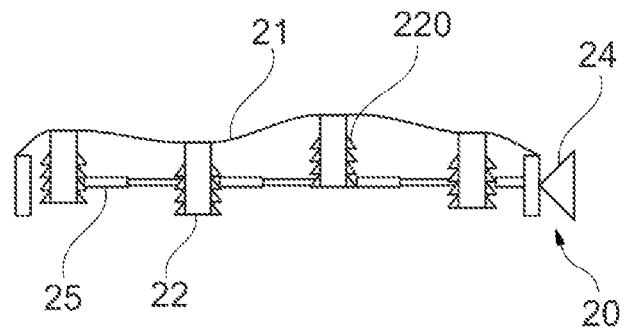
[Fig 4]
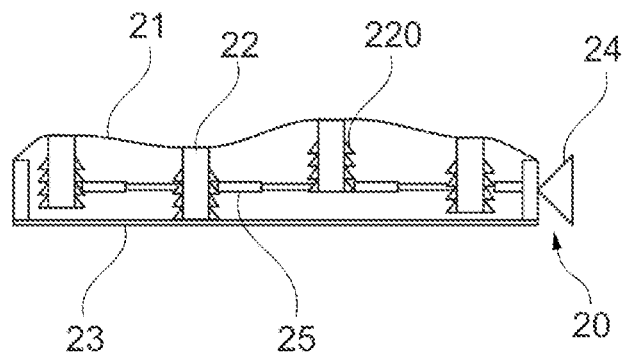
[Fig 5a]
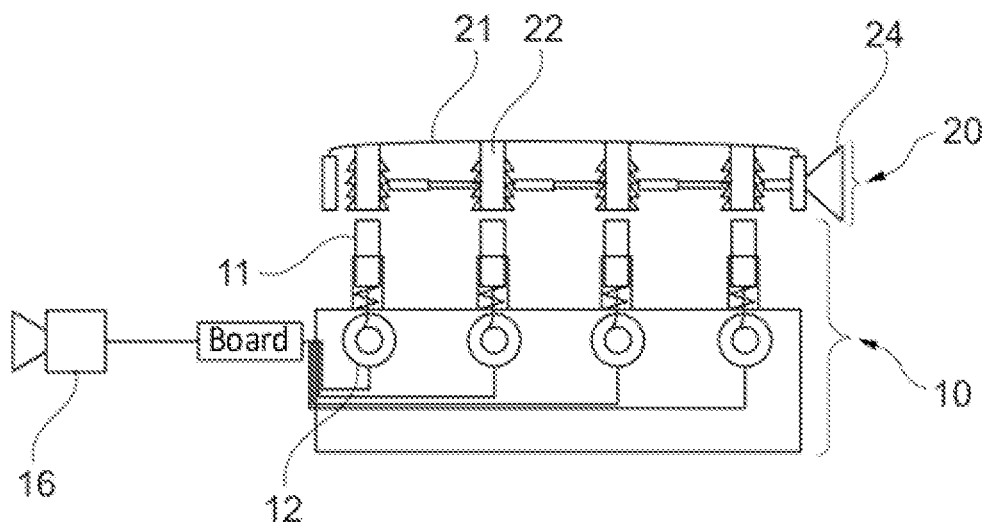

[Fig 5b]
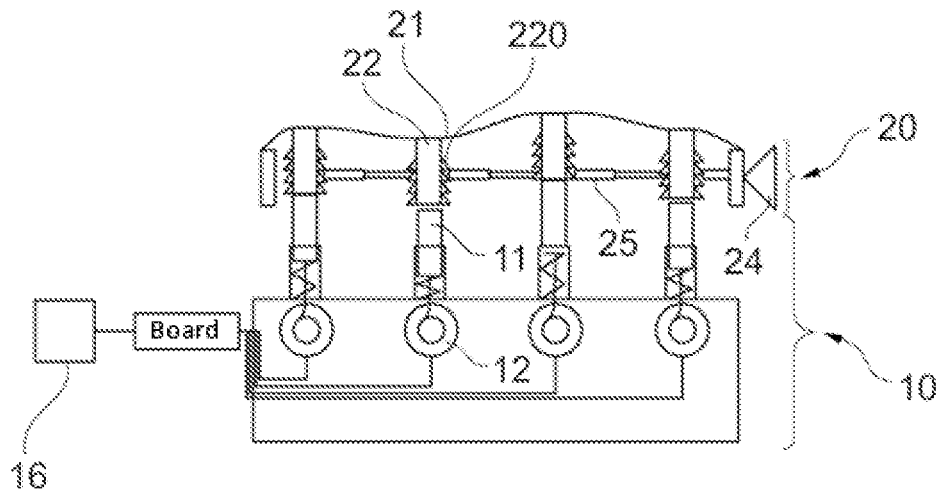
[Fig 6]
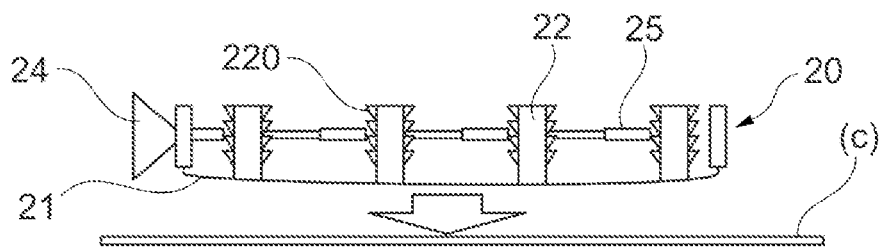
[Fig 7]
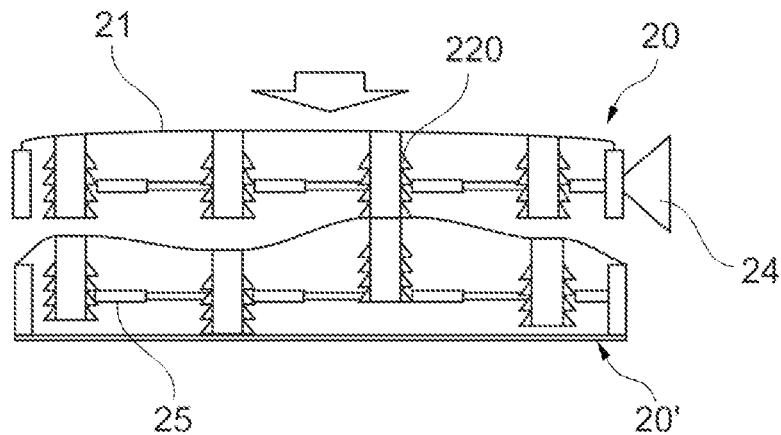

[Fig 8]
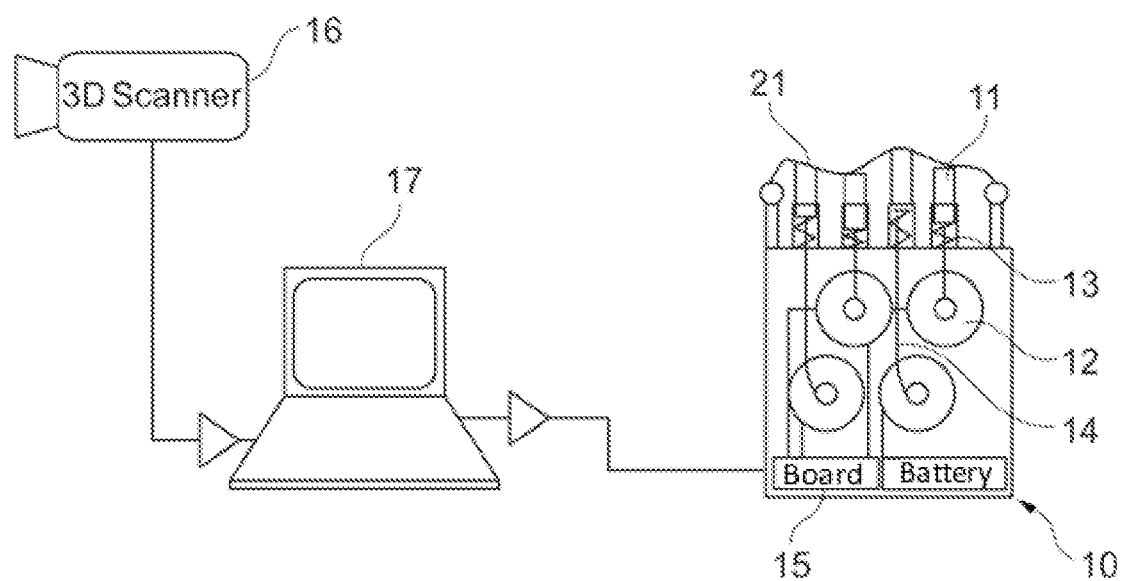
[Fig 9]
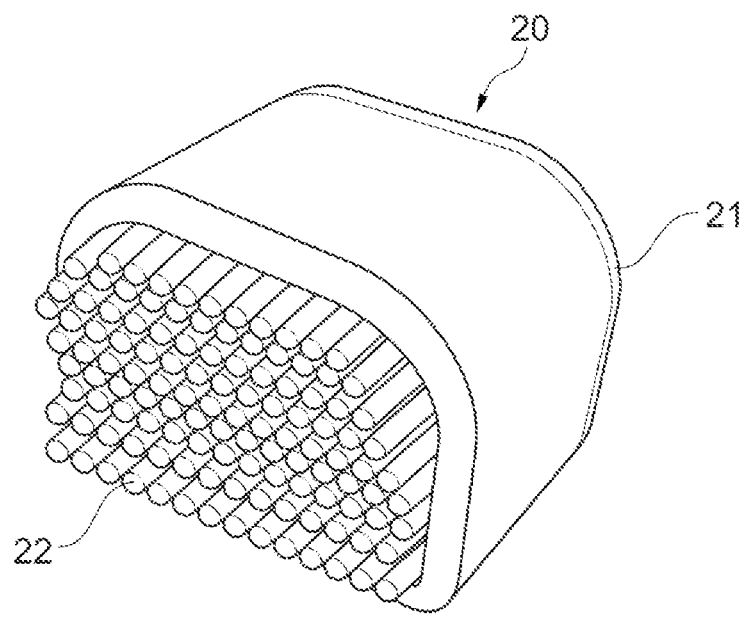

[Fig 10]
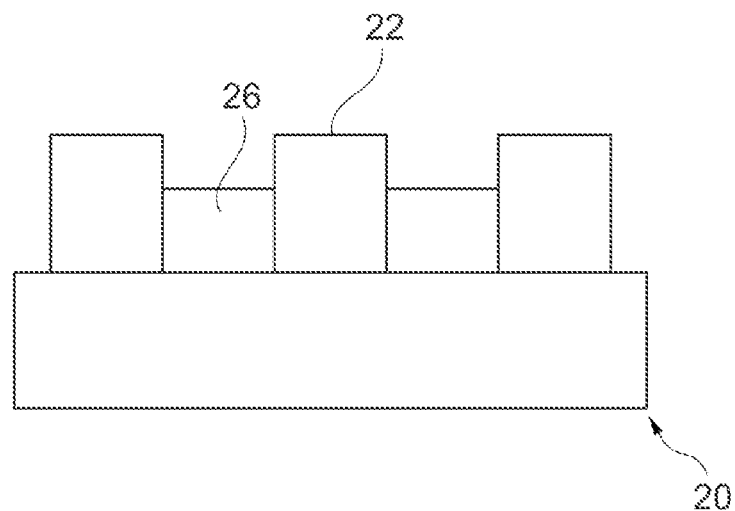
[Fig 11]
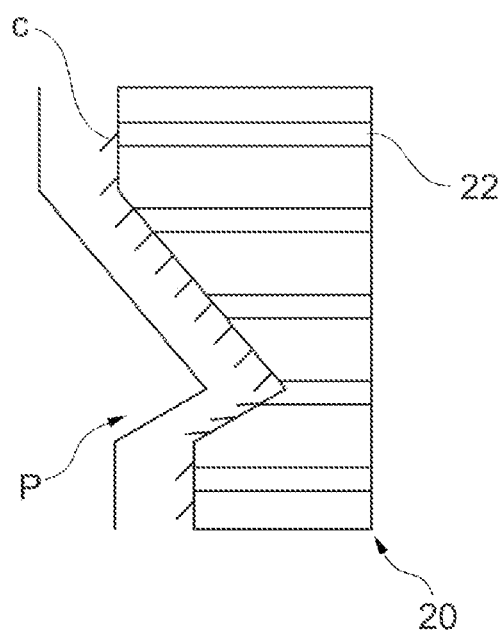

METHOD FOR SHAPING AN APPLICATOR FOR APPLYING A COSMETIC COMPOSITION

TECHNICAL FIELD

The present invention relates to a method for shaping an applicator for applying a cosmetic composition, in particular make-up, to a predefined region of the keratin materials of a user, in particular a region of skin. The invention also relates to a device used in such a method and to the cosmetic treatment, in particular make-up, methods that use them.

BACKGROUND

Many people seek to find the make-up which suits them best. They may choose from a large number of make-up products which they will subsequently be able to apply to a region of their face or of their body.

It is possible to produce, using known make-up products, numerous make-up effects, in particular on the eyelids, but these are rather limited to single flat colour tints, or to a gradient based on two or three colours. In both cases, a coloured fluid or powder is applied by finger or using an applicator, for example a brush, and is spread by smudging.

However, in using a finger or an applicator, such as a brush, it is difficult to achieve complex patterns on the face, in particular in recessed regions such as the region of the eyes, but also raised regions such as for example the cheeks. The morphology of the person should also be taken into account for the pattern to be applied correctly.

One notable problem lies in simply applying a pattern that follows the personal morphology of the user.

Application WO 2015/097613 describes a method for applying make-up to a region of human keratin materials using a make-up device that includes a deformable substrate having a transfer surface intended to receive a cosmetic ink deposited via a digital printer and to come into contact with the keratin materials, the substrate being pressed against an imprint of the support through the action of deformation means such as pressure before bringing the transfer surface into contact with the region to be made up. Such a device is relatively complex in structure.

Another solution to this problem consists in creating a series of applicators and then, one by one, searching for the one which is best suited by testing them on a user. This is a time-consuming operation and a make-up composition has to be used for each test. Thus, when it is observed that the make-up composition is applied uniformly, the applicator may be selected. If it is observed that the make-up composition is transferred partially, the make-up has to be removed from the region before testing another applicator. These operations, besides being time-consuming, are also expensive because they require the presence of a person to assist the user and to perform the tests to determine the applicator which suits them best.

In order for a user to be able to have an applicator that is suited to their personal morphology, another approach consists in using a means for acquiring a shape in three dimensions, such as a 3D scanner, and a means for producing 3D objects, such as a 3D printer. The slowness of these makes the operation too time-consuming for the user to leave with the object. It thus has to be produced then dispatched in a second step. Additionally, there is a need for a technician capable of running the operations of scanning, processing the scan and controlling the 3D printer. This approach therefore requires a technician to be employed on a permanent basis, which makes the operation complex and expensive.

Another approach consists in moulding a material capable of setting solid, such as plaster for example, on the face. However, it is not pleasant to feel such a material being applied to the face, in particular in the region of the eyes. Additionally, the operation is time-consuming and, as above, requires a skilled person to be employed to carry it out.

DISCLOSURE OF THE INVENTION

Consequently, there is a need to further improve the making up of human keratin materials, in particular for producing patterns, especially on the face, including in regions exhibiting raised areas, precisely and easily, without risking the deterioration of said patterns, and without having to employ special personnel.

The invention aims in particular to meet this need.

SUMMARY OF THE INVENTION

Thus, one subject of the invention is a method for shaping an applicator for applying a cosmetic composition to a predefined region of the keratin materials of a user, the applicator defining an application surface, the method using a shaping system comprising one or more movable elements and topographical data from an operation of acquiring, preferably digitally, the topography of at least a portion of said predefined region, in which method the shaping system automatically positions the one or more movable elements at least according to the topographical data, the positioning of the one or more movable elements imposing a shape to the application surface of the applicator.

By virtue of the invention, it is possible to modify an applicator that is initially of standard shape in order to obtain an applicator of personalized shape matched to the morphology of the user.

The term "keratin materials" refers to the skin, including the scalp, the lips, the nails, the hair and the eyebrows, and preferably the lips or the facial skin, in particular that of the eyelids or of the cheeks.

The personalized shape of the applicator may correspond to a shape that is complementary to the region to be made up. Thus, the surface of contact between the applicator and the region to be made up of the user is maximal and optimal.

Once the applicator is in the personalized configuration, its shape is advantageously not changed under the effect of application to the predefined region.

In one embodiment, the shaping system subjects a deformable portion of the applicator, in particular a membrane, to a deformation imposed by the one or more movable elements according to the position taken by said elements on the basis of the topographical data, the shape of the application surface being imposed by that of the deformable portion.

The deformable portion of the applicator may be a membrane made of an elastically deformable material, in particular rubber. It may also be a foam. These materials, which are easily able to deform elastically, make it easy to give the application surface the desired shape. Where appropriate, this deformable portion is removable and may be replaced before each use for hygiene reasons.

To hold it in place, the deformable portion may be crimped over the sides of the device, or attached otherwise, in particular removably or irremovably.

In another embodiment, the shaping system positions one or more of the movable elements of the applicator, bearing a deformable portion, in particular a membrane, according to the positioning of the one or more movable elements of the shaping system on the basis of the topographical data, the deformable portion undergoing a deformation imposed by the one or more movable elements of the applicator, the shape of the application surface being imposed by that of the deformable portion.

Acquiring the Topographical Data

The topographical data used in the method according to the invention are preferably from a 3D scan of at least a portion of said predefined region, the scan being performed in particular using one or more cameras, with, where appropriate, structured light projected onto said region.

The use of a 3D scan to acquire the topographical data has the advantage of being fast. Additionally, this mode of acquisition is not unpleasant for the user, unlike other solutions such as for example those making a mould using plaster.

The shaping system may be configured to acquire the topography of at least a portion of said predefined region. This embodiment allows an acquisition system to be integrated into the shaping system. A single circuit board may thus be used.

As a variant, the shaping system is linked to a remote device that includes means for acquiring the topography of at least a portion of said region. This embodiment allows the operations of acquiring the topography of a region and of deforming an applicator to be performed in parallel. In the case that the device is used in a shop or salon, it is then possible to perform these two operations on two separate customers at the same time. This allows a greater number of personalized applicators to be produced in a given time.

The shaping system may be linked to a server that includes a memory containing said topographical data. This server allows the topographical data of users to be saved so as to be able to use them again. This allows applicator shapes to be fine-tuned or new, identical applicators to be reproduced.

This possibility is particularly useful when the shape of the applicator, after modification thereof, is not fixed. Thus, in the case that this device is used in a beauty salon, the user may store their topographical data on the server so as not to have to perform the acquisition operation again on a subsequent visit. The topographical data may be indexed by the name of each user, or any other identifier, allowing it to be retrieved on another visit.

Processing the Topographical Data

Advantageously, the shaping system calculates the shape to be given to the application surface of the applicator on the basis of said topographical data.

The shape imposed to the application surface of the applicator may correspond to the inverse of the shape of the predefined region that is intended to receive the composition, i.e. the application surface may exhibit a relief that is the inverse of the relief of the region to be made up. For example, if the region to be made up exhibits a domed relief, the application surface will advantageously have a recessed relief.

Advantageously, the shape to be given to the application surface on the basis of said topographical data is calculated by software remotely from a workstation to which said data have been transmitted over a telecommunications network, in particular the Internet or a telephony network. This makes it possible in particular to benefit from more computing power and therefore to be able to produce the applicator faster.

The method may include displaying the topographical data and/or the resulting shape to be given to the application surface of the applicator on a screen.

Displaying these data makes it possible to check that there has been no error in the 3D scan which would result, for example, in a shape which does not correspond to the morphology of the user. Displaying in this way therefore prevents errors without having to produce the applicator in order to become aware of them.

The resulting shape to be given to the application surface may be stored for later use.

As a variant, the shape imposed to the application surface is determined on the basis of said topographical data to which at least one transformation has been applied, in particular a translation or a homothety.

This possibility of transforming the data allows the shape to be given to the applicator to be corrected, in particular to correct a defect, for example asymmetry in a region of the face, or to enlarge or reduce a region, in particular the lips.

On the basis of the operation of determining a shape to be imposed to the application surface, the calculation of a symmetrical shape may be carried out and applied by the shaping system, in particular for the application of the cosmetic composition to the eyelids.

It is thus possible to determine the topographical data for a region which is the mirror image of a region for which the topographical data have already been acquired. For example, based on the 3D scan of an eye, the system may determine the 3D file corresponding to the inverse of this eye.

Cosmetic Composition

The step of shaping the applicator may be preceded by a step of collecting a cosmetic composition that takes the form in particular of a transferable print or of a layer of powder, containing in particular pigments.

The cosmetic composition may equally be taken up after the shaping of the applicator.

Taking it up before the shaping step, i.e. when the applicator is substantially flat, makes it possible to correctly transfer complex patterns to the keratin materials, which is not possible when the cosmetic composition is taken up with an applicator, the shape of which has already been adapted to the morphology of the region to be made up.

The applicator may be loaded with cosmetic composition, fully or partly, by being brought into contact with a material soaked with the cosmetic composition, such as a pad. This pad is advantageously domed on its surface intended to come into contact with the application surface, so as to adapt to the shape of the applicator. In alternative forms, the applicator is loaded with composition directly by means of a block of composition, alternatively of a flocked applicator, of a brush or any other application means impregnated with composition.

As an alternative, the applicator is designed to deliver the cosmetic composition intended to be applied to the keratin materials and may comprise a reservoir attached on its back. In an alternative, the applicator is mounted on a reservoir at a later time.

The cosmetic composition may take the form of a transferable print or of a layer of powder, containing in particular pigments.

The cosmetic composition may be deposited on the transfer surface in the form of printed coloured patterns. The print may be made on a film made of plastic material.

In the case of a print, the printer may be a digital printer, in particular a laser printer arranged to allow the formation by electrophotography or magnetophotography of a layer of composition having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood to mean a pulverulent cosmetic composition that is compatible with the formation of an image via an electrophotographic or magnetophotographic process as used in laser printers. The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

The laser printer may have a deactivated fuser.

In some variants, the printer is an inkjet printer, for example a thermal or piezoelectric inkjet printer, or a sublimation printer.

In the case of a cosmetic composition in the form of a transferable print, the print may be made in the form of raster spots so as to form a halftone image, for example a monochromatic or polychromatic image.

The pattern formed by printing may be of any type. This pattern may reproduce the appearance of relief and/or colour heterogeneities of the skin, for example freckles or a mole. The pattern obtained by printing may comprise several areas of different colours. As a variant, the pattern obtained by printing is a flat colour tint.

The cosmetic composition may be in fluid or pulverulent form when borne by the application surface and before application to the keratin materials.

When it is fluid, the cosmetic composition has, for example, a viscosity ranging from 1 mPa·s to 500 mPa·s and preferably from 1 mPa·s to 300 mPa·s at 25° C.

The viscosity of a composition used in the invention may be measured via any method known to those skilled in the art, and in particular according to the following conventional method. At 25° C. using a Rheomat 180 viscometer, equipped with a spindle rotating at 200 rpm, a person skilled in the art can select the spindle for measuring the viscosity from the spindles M1, M2, M3 and M4 on the basis of his general knowledge, so as to be able to perform the measurement.

The cosmetic composition may take the form of a transferable print corresponding to a layer of powder, containing in particular pigments, or to a thickness of fluid, deposited by inkjet for example, containing one or more dyes and/or one or more pigments.

The cosmetic composition may comprise one or more colourants chosen from water-soluble dyes, liposoluble dyes, pulverulent colourants such as pigments, organic lakes, nacres, and glitter flakes, or colouring polymers.

The term "pigments" should be understood to mean white or coloured, mineral or organic particles of any form, which are insoluble in the cosmetic medium, and which are intended to colour the cosmetic composition.

The term "organic lakes" should be understood to mean particles formed from a dye attached to a substrate.

The term "nacres" should be understood to mean iridescent particles of any form, in particular produced by certain molluscs in their shell, or else synthesized.

The pigments may be white, black or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

Among the organic pigments that may be mentioned are carbon black, pigments and lakes of D & C type and lakes based on cochineal carmine or on barium, strontium, calcium or aluminium.

The nacres may be chosen from white nacres such as mica coated with titanium or with bismuth oxychloride, coloured nacres such as titanium mica coated with iron oxides, titanium mica coated in particular with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

Among the liposoluble dyes, mention may be made of Sudan Red III (CTFA: D&C Red 17), lutein, quinizarine green (CTFA: D&C Green 6), alizurol purple SS (CTFA: D&C Violet no. 2), Sudan Brown, DC Yellow 11, DC Orange 5, quinoline yellow, curcumin, and carotenoid derivatives such as lycopene, beta-carotene, bixin or capsanthin, and mixtures thereof. The colouring polymers are generally copolymers based on at least two different monomers, at least one of which is a monomeric organic dye. Such polymeric dyes are known to those skilled in the art. Reference may be made, for example, to the following documents: U.S. Pat. No. 5,032,670; 4,999,418; 5,106,942; 5,030,708; 5,102,980; 5,043,376; 5,104,913; 5,281,659; 5,194,463; 4,804,719; WO 92/07913 or EP 1 048 282.

The cosmetic composition may comprise one or more colourants, in particular photochromic pigments, i.e. colorants which have the property of changing colour when they are irradiated with a light source of a certain frequency, and then of regaining their initial colour, or a similar colour, when the irradiation is stopped. Among the photochromic colorants, mention may be made in particular of:

complex mineral photochromic compounds and more particularly doped aluminosilicates and metal oxides and metal oxide hydrates, such as those described in WO-A-02/36083;

photochromic naphthopyran compounds, in particular 3H-naphtho[2,1-b]pyrans or 2H-naphtho[1,2-b]pyrans, for instance 3,3-bis(4-methoxyphenyl)-6-morpholino-3H-naphtho [2,1-b]pyran, 3-phenyl-3-(4-morpholinophenyl)-6-morpholino-3H-naphtho [2,1-b]pyran, 3-phenyl-3-(4-piperidinophenyl)-6-morpholino-3H-naphtho[2,1-b]pyran, 3-phenyl-3-(4-piperidinophenyl)-6-carboxymethyl-9-N-dimethyl-3H-naphtho[2,1-b]pyran or 2-phenyl-2-(4-piperidinophenyl)-5-carboxymethyl-9-N-dimethyl-2H-naphtho[1,2-b] pyran. Such compounds are described in patent application EP-A-1 410 785;

diarylethene or fulgide compounds such as those described in patent application EP-A-938 887.

The cosmetic composition may also comprise one or more fillers, in particular in a content ranging from 0.01% to 50% by weight, relative to the total weight of the composition, preferably ranging from 0.01% to 30% by weight.

The term "fillers" should be understood to mean colourless or white, mineral or synthetic particles of any shape, which are insoluble in the medium of the composition, irrespective of the temperature at which the composition is manufactured. These fillers serve especially to modify the rheology or texture of the composition.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, polyamide powder (Nylon) (Orgasol from Atochem), poly-β-alanine powder and polyethylene powder, powders of tetrafluoroethylene polymers (Teflon), lauroyllysine, starch, boron nitride, hollow polymer microspheres such as those of polyvinylidene chloride/acrylonitrile, for instance Expancel (Nobel Industrie), or of acrylic acid copolymers (Polytrap from the company Dow Corning) and silicone resin microbeads (for example Tospearls from Toshiba), elastomeric polyorganosiloxane particles, precipitated calcium carbonate, magnesium carbonate, magnesium hydrocarbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The cosmetic composition may also include an additional polymer such as a film-forming polymer. The term "film forming polymer" is understood to mean a polymer that is capable of forming, by itself or in the presence of an auxiliary film-forming agent, a continuous film that adheres to a support, in particular to keratin materials. Among the film-forming polymers that may be used in the composition, mention may be made of synthetic polymers, of radical type or of polycondensate type, polymers of natural origin and mixtures thereof, in particular acrylic polymers, polyurethanes, polyesters, polyamides, polyureas, and cellulose-based polymers, for instance nitrocellulose.

When the composition is based on a cosmetic toner such as described above, this toner may comprise, besides a colouring agent, a compound for controlling the electrical charge, a particular additional filler, a lubricant, a wax and/or a binder. Preferably, the particles of the toner have a mean size of between 1 and 16 µm. The toner comprises, for example, pigments with a particle size of between 1 and 10 µm.

The composition may include both a hydrophilic phase comprising one or more compounds that are miscible with water at 20° C. and an oily phase comprising one or more water-immiscible compounds.

At an ambient temperature of 20° C., the hydrophilic phase may form a dispersed phase in a continuous phase formed by the oily phase; a water-in-oil (W/O) emulsion is thus obtained. In one variant, the oily phase forms at 20° C. a dispersed phase in a continuous phase formed by the hydrophilic phase; an oil-in-water (O/W) emulsion is thus obtained. The hydrophilic phase and/or the oily phase may each include one or more colorants.

The composition may include a surfactant in order to obtain an oil-in-water emulsion, or a water-in-oil surfactant. It may thus be chosen from hydrocarbon-based or silicone surfactants, the HLB of which will be chosen according to the desired direction of emulsion, for example less than 8 for W/O emulsions, advantageously from 3 to 7, and for example greater than or equal to 8 for direct emulsions.

Examples of silicone surfactants that may be mentioned are those of the alkyldimethicone copolyol type and of the dimethicone copolyol type.

Examples of non-silicone surfactants that may be mentioned are non-ionic surfactants such as the (poly)oxyalkylenated (C2-C3 alkyl), (poly)glycerolated derivatives of alcohols, of esters, of ethers comprising at least one hydrocarbon-based group with at least 10 carbon atoms, potentially (poly)oxyalkylenated, (poly)glycerolated sorbitan esters or ethers; alkyl polyglucosides and mixtures thereof.

The anionic surfactants may be chosen for example from alkyl (ether) sulfates, sulfonates, (alkyl)phosphates, salts, in particular metal salts, of C10-C30 acids; these surfactants comprising at least one hydrocarbon-based group with at least 10 carbon atoms which may or may not be (poly) oxyalkylenated (C2-C3 alkyl); and mixtures thereof.

The one or more compounds of the oily phase may have a solubility in water at 25° C. of less than 5% by weight.

The one or more compounds of the oily phase may be chosen from the oils usually used in cosmetics, which may be chosen from natural or synthetic, hydrocarbon-based, silicone or fluoro oils, which are optionally branched, alone or as a mixture.

The term "non-volatile oil" is understood to mean an oil that is capable of remaining on the skin at ambient temperature and atmospheric pressure for at least one hour, and in particular having a non-zero vapour pressure at ambient temperature (25° C.) and atmospheric pressure of less than 0.01 mmHg (1.33 Pa).

Mention may in particular be made of non-volatile hydrocarbon-based oils, in particular of plant, mineral, animal or synthetic origin, such as liquid paraffin (or petroleum jelly), squalane, hydrogenated polyisobutene (Parleam), perhydrosqualene, macadamia oil, soybean oil, sweet almond oil, beauty-leaf oil, palm oil, grapeseed oil, sesame oil, corn oil, arara oil, rapeseed oil, sunflower oil, cotton oil, apricot oil, castor oil, avocado oil, jojoba oil, olive oil or cereal germ oil, shea butter oil; linear, branched or cyclic esters containing more than 6 carbon atoms, notably 6 to 30 carbon atoms, such as esters of lanolic acid, of oleic acid, of lauric acid or of stearic acid; esters derived from long-chain acids or alcohols (i.e. containing from 6 to 20 carbon atoms), especially the esters of formula RCOOR' in which R represents the higher fatty acid residue comprising from 7 to 19 carbon atoms and R' represents a hydrocarbon-based chain comprising from 3 to 20 carbon atoms, in particular C12-C36 esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, and glyceryl or diglyceryl triisostearate; higher fatty acids, especially of C14-C22, such as myristic acid, palmitic acid, stearic acid, behenic acid, oleic acid, linoleic acid, linolenic acid or isostearic acid; higher fatty alcohols, especially of C16-C22, such as cetanol, oleyl alcohol, linoleyl alcohol or linolenyl alcohol, isostearyl alcohol or octyldodecanol; and mixtures thereof.

Mention may also be made of decanol, dodecanol, octadecanol, liquid fatty acid triglycerides of 4 to 10 carbon atoms such as heptanoic or octanoic acid triglycerides, caprylic/capric acid triglycerides; linear or branched hydrocarbons of mineral or synthetic origin such as liquid paraffins and derivatives thereof, petroleum jelly, polydecenes and hydrogenated or non-hydrogenated polyisobutenes such as Parleam; synthetic esters and ethers in particular of fatty acids, for instance purcellin oil, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate or fatty alcohol heptanoates, octanoates and decanoates; polyol esters such as propylene glycol dioctanoate, neopentyl glycol diheptanoate or diethylene glycol diisononanoate; and pentaerythritol esters; fatty alcohols containing from 12 to 26 carbon atoms, such as octyldodecanol, 2-butyloctanol, 2-hexyldecanol or 2-undecylpentadecanol.

Among the non-volatile silicone oils, mention may be made of non-phenyl silicones, such as in particular polysiloxanes (also known as dimethicone). Also suitable are phenyl silicones (in other words silicones that comprise at least one phenyl substituent), such as for example phenyl trimethicones, trimethyl pentaphenyl trisiloxanes, tetramethyl tetraphenyl trisiloxanes, diphenyl dimethicones, trimethylsiloxyphenyl dimethicones and diphenylsiloxyphenyl trimethicones, alone or as mixtures.

Among the volatile compounds, mention may be made of non-silicone volatile oils, in particular C8-C16 isoparaffins, such as isododecane, isodecane and isohexadecane.

Linear or cyclic, but preferably linear, volatile silicone oils may also be suitable, such as in particular decamethyl tetrasiloxane, dodecamethyl pentasiloxane and mixtures thereof.

More preferentially, mention may be made of volatile or non-volatile alkanes that are liquid at ambient temperature, and more particularly decane, heptane, dodecane, isododecane, isohexadecane, cyclohexane and isodecane, and mixtures thereof.

Among the preferred compounds of the oily phase, examples that may be mentioned include isododecane (boiling point: 180° C.), isopropyl myristate (boiling point: 168° C.), isostearyl alcohol (boiling point: 331° C.), isodecyl neopentanoate (boiling point: 272° C.), isononyl isononanoate (boiling point: 285° C.), oleyl alcohol (boiling point: 315° C.), 2-octyldodecanol (boiling point: 358° C.), isopropyl palmitate (boiling point: 340° C.), isopropyl isostearate (boiling point: 361° C.), and mixtures thereof.

The oil may be present in the composition in a content ranging from 2% to 60% by weight, preferably ranging from 2% to 40%, preferably ranging from 15% to 70% and particularly preferably ranging from 2% to 25%, relative to the total mass of the composition.

The oily phase may also comprise substances that are solid at ambient temperature, such as waxes.

The term "wax" is understood to mean a lipophilic compound, which is solid at ambient temperature (25° C.), with a reversible solid/liquid change of state, with a melting point of greater than or equal to 30° C., which may be up to 120° C. By bringing the wax to the liquid state (melting), it is possible to make it miscible with the oils that may be present and to form a microscopically homogeneous mixture, but on returning the temperature of the mixture to ambient temperature, recrystallization of the wax in the oils of the mixture is obtained. The melting point of the wax may be measured using a differential scanning calorimeter (D.S.C.), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C. As waxes that may be used in the composition, mention may be made of beeswax, carnauba wax or candelilla wax, paraffin, microcrystalline waxes, ceresin or ozokerite; synthetic waxes such as polyethylene waxes or Fischer-Tropsch waxes, silicone waxes such as alkyl or alkoxy dimethicones containing from 16 to 45 carbon atoms.

The nature and amount of the waxes depend on the desired mechanical properties and textures. As a guide, the composition, in particular in emulsion form, may contain from 0.01% to 30% by weight and better still from 1% to 20% by weight of waxes relative to the total weight of the cosmetic composition.

Locking the Applicator

The step of shaping the applicator of the method according to the invention may be followed by a step of locking the shape of the applicator and/or of the shaping system.

The shape of the applicator may thus be fixed once changed, and the change in its shape may be irreversible. This locking operation makes it possible to ensure that the shape of the applicator is not changed under the effect of application to the region of keratin materials. Depending on the locking method used, the applicator may or may not be reconfigurable. The term "reconfigurable" is understood to mean that it is possible to return the applicator to a standard shape after it has been shaped and used for making up a predefined region.

This locking step may be performed by pouring an adhesive material between the movable elements of the applicator and/or those of the shaping system. In this case, the applicator is not reconfigurable, it cannot return to its initial shape and then be adapted again to the morphology of another region or of another user. However, it is possible to produce a personalized shape which is suitable for a plurality of users.

In one variant, the applicator including movable elements provided with teeth, the locking step is performed by positioning one or more movable bolts in the teeth of the movable elements of the applicator. The shape given to the applicator may be reconfigured by removing the one or more movable bolts from the teeth. Using this method, the applicator is reconfigurable. The user is then free to change the shape of the applicator as desired by using the device according to the invention. This is in particular useful when the applicators are used in a beauty salon. Specifically, in that case, it is possible to use a single applicator and to adapt it to each new user. The applicator may thus be shared by different people, which makes it possible to limit costs since just one applicator may be used for several clients.

A reconfigurable applicator also makes it possible to use one and the same applicator to make up different regions. For example, one and the same applicator may be used to make up the eyes, the cheeks, the lips or the nails, its shape changing from one region to the other. Lastly, the possibility of reconfiguring the applicator allows the operation of adjusting the shape of the applicator to be started again in the event of an error.

The applicator may be adapted by virtue of the device according to the invention to take two shapes: a morphological shape and a non-morphological special shape. This special shape may be a planar shape, or an outwardly convex shape. This shape may be useful in particular for more easily collecting the make-up composition which will subsequently be applied. Advantageously, it is taken up with the applicator in its special shape and applied with the applicator in its morphological shape.

As a variant, a shape is imposed to a first device by positioning the one or more movable elements of the shaping system at least on the basis of the topographical data, and this first device is used to shape an applicator by positioning it on top, the applicator including in particular one or more movable elements bearing a deformable portion that defines an application surface.

Moulding

The shaping system may be used by using the topographical data as the basis for forming a mould.

The mould may be used as an applicator for a cosmetic composition.

In this case, care is taken that the shaping system, on which the mould is formed, reproduces the morphology of the face in its true form and not its inverse form. A cosmetic composition may then be deposited inside the mould and the mould is then pressed against the region to be made up.

As a variant, the mould may be used to impose its shape to the application surface of an applicator. In this case, care is taken that the shaping system, on which the mould is formed, takes the inverse morphology of the face. It is therefore not necessary to use a shaping system each time.

Using a mould avoids having to save the topographical data. Specifically, instead of returning the shaping system to the desired shape and then placing the applicator thereon, the deformable portion or the movable elements of the applicator are placed against the mould to give the desired shape.

The material used to form the mould may be plaster, or a photo-crosslinkable or reactive material.

The shape to be given to the mould may be adjusted, for example by adding or removing material.

Cosmetic Treatment Method

Another subject of the invention, according to another of its aspects, is a method for the cosmetic treatment of a predefined region of the keratin materials of a user, in particular for applying make-up to same, including the application of a cosmetic composition to said predefined region using the application surface of an applicator shaped by means of the method according to the invention.

Device

Another subject of the invention is a device for shaping an applicator for applying a cosmetic composition, in particular make-up, to a predefined region of the keratin materials of a user, the applicator defining an application surface, the device including a system for shaping the applicator that comprises one or more movable elements, the shaping system being configured to automatically position the one or more movable elements at least on the basis of topographical data from a prior operation of acquiring, preferably digitally, the topography of at least a portion of said predefined region, the shape of the application surface of the applicator being dependent on the positioning of the one or more movable elements.

The one or more movable elements of the shaping system may include movable mechanical connections, such as actuating rods, that link a deformable portion, which may be used to impose the shape of the application surface, to one or more actuators, in particular electric, hydraulic or pneumatic actuators. Each movable element may be linked to a return element, allowing the movable element to be moved away from or brought closer to the support of the shaping system. A cable may link each movable element to an actuator. To bring a movable element closer to the support of the shaping system, the actuator advantageously rotates in one direction such that the cable 1 is wound up and pulls on said movable element, the return element then being compressed. Conversely, to move the movable element away from the support of the shaping system, the actuator advantageously rotates in one direction such that the cable is unwound, and the return element relaxes, moving the movable element away from the support of the shaping system.

The presence of a plurality of actuators allows the shaping system to be driven precisely at a plurality of points so as to obtain a shape of personalized applicator that is closer to that desired and that best suits the morphology of the user.

The shaping system of the device may be configured, where appropriate, also to be able to be actuated manually in order to adjust the shape to be given to the application surface. This allows the shaping system to be adjusted so that it takes exactly the desired shape. In particular, this feature allows the shape of the applicator to be rectified if that is desired by the user, in particular according to the desired make-up effect or for rectifying a defect in the region to be made up.

Advantageously, the shaping system includes between 0.5 and 25 movable elements per square centimetre of surface, preferably between 1 and 16 movable elements per square centimetre of surface.

Set

Another subject of the invention, according to another of its aspects, is a cosmetic set including, within the same packaging, a device for shaping an applicator according to the invention, and at least one applicator for applying a cosmetic composition, in particular make-up, to a predefined region of the keratin materials of a user.

The applicator of the set may include a deformable portion, in particular a membrane made of an elastically deformable material.

The applicator of the set may include one or more movable elements bearing the deformable portion, the shape of said deformable portion being dependent on the positioning of the one or more movable elements imposed by the positioning of the movable elements of the shaping device.

The set may include a cosmetic composition that takes the form in particular of a transferable print or of a layer of powder, containing in particular pigments.

The features described above with respect to the shaping method apply to the cosmetic treatment method, to the device and to the set, and vice versa.

BRIEF DESCRIPTION OF THE DRAWINGS

The invention will be better understood from reading the following detailed description of non-limiting embodiments thereof and from studying the attached drawing, in which:

FIG. 1 shows an exemplary system for shaping a membrane according to the invention, from the side;

FIG. 2 shows the shaping system of FIG. 1, from above;

FIG. 3 shows an exemplary applicator that can be reconfigured;

FIG. 4 shows an exemplary applicator that cannot be reconfigured;

FIGS. 5a and 5b illustrate an example of shaping an applicator according to the method that is the subject of the invention;

FIGS. 6 and 7 illustrate the shaping of an applicator according to one particular embodiment of the invention;

FIG. 8 shows an assembly including a 3D capture system, a computer, an exemplary shaping system according to the invention and an applicator;

FIG. 9 shows another exemplary deformable applicator that is usable with a shaping system according to the invention;

FIG. 10 shows an applicator fixed with an adhesive material;

FIG. 11 illustrates the application of a cosmetic composition using an applicator shaped by means of a method according to the invention.

DETAILED DESCRIPTION

FIGS. 1 and 2 illustrate an exemplary shaping system 10 according to the invention, configured to shape the application surface of an applicator on the basis of topographical data of at least a portion of a predefined region of the keratin materials of a user. This shaping operation makes it possible to match the application surface to the morphology of said predefined region for the application of a cosmetic composition.

In the example shown in FIGS. 1 and 2, the shaping system 10 includes two parallel rows of four movable elements 11, composed of actuating rods in this example. These movable elements each move only along an axis X, all in the same direction. Each movable element 11 is linked to a return element 13. A cable 14 links each movable element 11 to an actuator 12. To bring the movable element 11 closer to the support of the shaping system 10 along the axis X, the actuator 12 rotates in one direction such that the cable 14 is wound up and pulls on the movable element 11, the return element 13 then being compressed. Conversely, to move the movable element 11 away, the actuator 12 rotates in one direction such that the cable 14 is unwound. The return element 13 relaxes and moves the movable element 11 away from the support of the shaping system 10.

In the embodiment shown in FIG. 1, a 3D camera makes it possible to acquire topographical data of a predefined region of the keratin materials of a user, for example the region of an eye or of a cheek. These data are measurements of positions in space. Thus, each item of data represents one point on the face for which the coordinates in space are known. The overall set of data allows the shape of the acquired region of the face to be reproduced.

In the example in question, the shaping system 10 is connected to a circuit board 15 allowing the topographical data from the prior acquisition operation to be processed. This processing operation makes it possible to determine the movement along the axis X to be applied to each movable element 11 such that the movable elements 11 are positioned so as to reproduce the inverse shape of the region acquired previously. Thus, the difference in height between two movable elements 11 advantageously corresponds to the difference in height between two points on the face for which the data have been acquired.

Once the movable elements 11 have been positioned on the basis of the topographical data of the region to be made up, in the example described, a membrane 21, corresponding to the deformable portion of the applicator to be shaped, is placed over the shaping system 10. The positioning of the movable elements 11 imposes a shape to the membrane; in particular, the inverse of the region to be made up. Thus, the shape of the applicator is adapted to the morphology of the user.

FIGS. 3 and 4 show an applicator 20, the membrane 21 of which defines an application surface. This applicator includes movable elements 22 that impose a deformation to the membrane 21 of the applicator 20. These movable elements 22 are provided with teeth 220, associated with movable bolts 25 that allow the applicator to hold its shape.

An unlocking element 24 allows the movable bolts 25 to be removed from the teeth 220. Once the bolts have been removed from the teeth 220, the movable elements 22 return to their initial position and no longer impose the particular shape to the membrane 21. The applicator may thus be reconfigured.

FIGS. 5a and 5b illustrate the steps for shaping an applicator 20. In the first step, illustrated in FIG. 5a, the applicator 20 is placed on the shaping system 10. Each movable element 22, provided with teeth 220, of the applicator 20 rests on a movable element 11 of the shaping system 10.

In the second step, illustrated in FIG. 5b, the actuators 12 change the positions of the movable elements 11 in accordance with the topographical data acquired previously, as described above. The change in the positions of the movable elements 11 of the shaping system results in a change in the positions of the movable elements 22 of the applicator, the application surface of which may then take the inverse shape of the region to be made up. The applicator is advantageously locked in this configuration by pushing the locking element.

To proceed with applying make-up, the membrane 21 is brought into contact with a cosmetic composition C, then the membrane 21 of the applicator 20 is pressed onto the region to be made up P in order to transfer the cosmetic composition C to the keratin materials. This last step is shown in FIG. 11.

An exemplary applicator 20 that can be shaped by the shaping system 10 according to the invention is shown in FIG. 9. This applicator includes a membrane 21 and movable elements 22 without teeth. In this example, to fix the applicator 20, an adhesive material 26, which hardens by crosslinking, is poured between the movable elements 22, as illustrated in FIG. 10. The shape of the applicator 20 is then fixed and cannot be reconfigured.

Example 1

In a first example of use, described with reference to FIG. 8, the user uses the shaping system 10 according to the invention to give the inverse shape of the region to be made up to the application surface. Once the desired shape has been obtained, the user applies their make-up using the applicator.

In this embodiment, the shaping system 10 is produced with four stepper motors 12. The movable elements 11 include rods of about 5 mm in diameter, 30 mm in length, and which are spaced apart by about 3 mm.

In a first step, the topographical data of the region to be made up on the user, for example an eyelid, are captured using a 3D scanner 16.

These topographical data are transmitted to a computer server 17 that is configured to use the topographical data to calculate the positioning of the movable elements 11, which are subsequently moved in accordance with the calculation performed.

A membrane 21 is then placed over the set of movable elements 11, and it is crimped over the ends of the system 10.

The computer server 17 may in particular provide the shaping system 10 with a morphology of the face in inverse mode, i.e. a complementary morphology of the shape of the face. The actuators 12 then move the movable elements 11, and in so doing the membrane 21 takes the inverse shape of the portion of the face to be made up. The membrane 21 may then be used to apply make-up. For this, a layer of cosmetic composition, for example a layer of powder, is deposited on the application surface, and then brought into contact with the region to be made up.

To apply make-up, it is also possible to give a special shape to the membrane 21 before depositing a layer of cosmetic composition. In particular, the membrane 21 is transformed into a planar surface and it is brought into contact with a layer of cosmetic composition, and then the inverse shape of the region of keratin materials to be made up is given to the membrane 21 by placing it over the shaping system 10, as described above. Next, the membrane 21 is brought into contact with the region of keratin materials to be made up.

The cosmetic composition may be a transferable print or a layer of powder, containing in particular pigments. The invention makes it possible in particular to produce patterns on the keratin materials in a straightforward manner.

This mode of use of the shaping system 10 is particularly suitable for a beauty salon or shop for example. Specifically, this use allows a plurality of customers to be made up one after the other using the same applicator 20 while giving a personalized shape to the application surface 21, corresponding to each customer. Since the customers may return several times, in order for them to avoid having to go through a 3D acquisition operation on each visit, it is possible to store their morphologies and to index them by their name or any other identifier.

This mode of use is also applicable to a user who has a shaping system 10 according to the invention and an applicator 20 at home. In this case, the user may use the device to apply make-up to several parts of the face. The device captures and stores the inverse 3D shape of each region of keratin materials to be made up, for example the eyelids, the cheeks, the lips or the nails. The user then uses a single applicator 20, the shape of which they modify to adapt it to each region.

It is also possible to store the inverse 3D shapes of different people, for example different members of the same family, so that each of them may adapt the applicator 20 to their morphology.

It is also possible to use the device according to the invention in a hotel. For example, there may be a standard applicator 20 in each room and a shaping system 10 available from reception. Each client then has the possibility of coming to reception to adapt the applicator 20 to their morphology in order to apply their makeup.

Example 2

In another exemplary implementation, the user uses the shaping system 10 to adapt the shape of the application surface of a standard applicator 20 to their morphology. The shape of the surface of the applicator is therefore the inverse of the region to be made up on the user. The applicator 20 is then fixed so as to hold the personalized shape.

The applicator 20 may be fixed reversibly, in which case it may be reconfigured to return to a standard shape in order to be deformed anew. One possibility for fixing the applicator reversibly is to use a system of bolts 25 that are movable in relation to teeth 220 borne by the movable elements 22 of the applicator, as described above.

The applicator may also be fixed irreversibly, i.e. it can no longer take a shape other than that in which it has been fixed. One possibility for this is to pour an adhesive material which hardens by crosslinking, as described above.

Example 3

The following description is provided with reference to FIGS. 6 and 7.

In this example, in order to allow the user to take up the cosmetic composition using an applicator in a special shape and then to change the shape thereof, they are provided with an applicator 20, which has not been shaped, with a planar surface, and a first device 20' which is fixed and the shape of which is the inverse of the region of the keratin materials to be made up. The applicator 20 is for example an applicator which may be locked by means of a system of bolts that are movable in relation to teeth, as described above.

The user takes up the composition by pressing the application surface 21 of the applicator 20 onto a layer of cosmetic composition C. It is also possible to print a pattern directly onto the application surface 21. This step is illustrated in FIG. 6.

The user places the applicator 20 on the first device 20', the shape of which is the inverse of the region to be made up, as shown in FIG. 7. By pressing, the device 20' prints its shape into the applicator 20. The user then applies make-up with this applicator.

When the user wishes to apply make-up again, they reconfigure the applicator 20 by pulling the locking member 24 to give it a planar shape and go back to the first step.

It is also possible to envisage a step of cleaning the application surface in order to remove all trace of cosmetic composition for external application.

Preferably, the first device 20' is fixed to avoid mistakes. In particular, no locking member is provided and access to the actuating rods is prevented.

This embodiment is therefore economical because it does not require the user to buy a shaping system 10 or to make regular trips to a beauty salon. The invention also makes it possible to correctly transfer complex patterns to the keratin materials, which is not possible when the cosmetic composition is taken up with an applicator, the shape of which has already been adapted to the morphology of the region to be made up.

Alternatively, it is possible to make a mould of the inverse shape of the region to be made up and to use it to deform the applicator which is bearing the cosmetic composition, and which is initially in a special shape, for example planar. The mould may for example be made of plaster or of a photo-crosslinkable or reactive material.

In this case, the user makes the mould using a shaping system in a shop or salon. They also buy an unfixed applicator in a special shape. Using the mould and the applicator, they may simply take up a cosmetic composition and then adapt the shape of the applicator to their morphology.

The invention is not limited to the examples which have just been described.

Other types of movable elements and of application surfaces may be used, and other materials for producing them, or other means for moving the movable elements.

The invention claimed is:

1. A method for shaping an applicator for applying a cosmetic composition to a predefined region of the keratin materials of a user, the applicator defining an application surface, the method using a shaping system comprising one or more movable elements and topographical data from an operation of acquiring the topography of at least a portion of said predefined region, method comprising at least the following step: the shaping system automatically positions the one or more movable elements at least on the basis of the topographical data, the positioning of the one or more movable elements imposing a deformation to the application surface of the applicator.

2. The method according to claim 1, wherein the shaping system subjects a deformable portion of the applicator to a deformation imposed by the one or more movable elements according to the position taken by said elements on the basis of the topographical data, the shape of the application surface being imposed by that of the deformable portion.

3. The method according to claim 1, wherein the shaping system imposes a position to one or more of the movable elements of the applicator, bearing a deformable portion according to the positioning of the one or more movable elements of the shaping system on the basis of the topographical data, the deformable portion undergoing a deformation imposed by the one or more movable elements of the applicator, the shape of the application surface being imposed by that of the deformable portion.

4. The method according to claim 1, wherein the shaping system calculates the shape to be given to the application surface of the applicator on the basis of said topographical data.

5. The method according to claim 1, wherein the shape imposed to the application surface of the applicator corresponds to the inverse of the shape of the predefined region that is intended to receive the composition.

6. The method according to claim 1, wherein the shape imposed to the application surface is determined on the basis of said topographical data to which at least one transformation has been applied.

7. The method according to claim 1, wherein, on the basis of the operation of determining a shape to be imposed to the application surface, the calculation of a symmetrical shape is carried out and applied by the shaping system.

8. The method according to claim 1, further comprising using topographical data from a 3D scan of at least a portion of said predefined region of the keratin materials of the user, the scan being performed by one or more cameras and/or by projecting structured light onto said region.

9. The method according to claim 1, wherein the step of shaping the applicator being preceded by a step of collecting a cosmetic composition.

10. The method according to claim 1, wherein the shaping of the applicator is followed by a step of locking the shape of the applicator and/or of the shaping system.

11. The method according to claim 10, wherein the locking step being performed by pouring an adhesive material between the movable elements of the applicator and/or those of the shaping system.

12. The method according to claim 10, wherein the applicator including movable elements provided with teeth, the locking step being performed by positioning one or more movable bolts in the teeth of the movable elements of the applicator.

13. The method according to claim 12, wherein the shape given to the applicator is reconfigured by removing the one or more movable bolts from the teeth.

14. The method according to claim 1, wherein a shape is imposed to a first device by positioning the one or more movable elements of the shaping system at least on the basis of the topographical data, and wherein this first device is used to shape an applicator by positioning it on top.

15. The method according to claim 1, wherein the shaping system is used by using the topographical data as the basis for forming a mould.

16. The method according to claim 15, the mould being used as an applicator for a cosmetic composition.

17. The method according to claim 15, wherein the mould being used to impose its shape to the application surface of the applicator.

18. A method for the cosmetic treatment of a predefined region of the keratin materials of a user including the application of a cosmetic composition to said predefined region using the application surface of an applicator shaped by means of the method according to claim 1.

19. The method according to claim 1, wherein the acquisition of the topography of at least a portion of said predefined region is performed digitally.

20. The method according to claim 2, wherein the deformable portion of the applicator is a membrane.

21. The method according to claim 3, wherein the deformable portion of the applicator is a membrane.

22. The method according to claim 6, wherein said at least one transformation is a translation or a homothety.

23. The method according to claim 7, wherein the calculation of a symmetrical shape is carried out and applied by the shaping system for the application of the cosmetic composition to the eyelids.

24. The method according to claim 9, wherein the cosmetic composition takes the form of a transferable print or of a layer of powder.

25. The method according to claim 24, wherein the cosmetic composition contains pigments.

26. The method according to claim 14, wherein the applicator includes one or more movable elements bearing a deformable portion that defines an application surface.

27. The method according to claim 18, wherein the cosmetic treatment is for applying make-up to said predefined region of the keratin materials of a user.

* * * * *